US012759977B2

(12) United States Patent
Chen et al.

(10) Patent No.: US 12,759,977 B2
(45) Date of Patent: Oct. 13, 2026

(54) PYRROLINONE COMPOUND AND METHOD FOR PREPARING THE SAME

(71) Applicant: WUHAN JIANMIN DAPENG PHARMACEUTICAL CO., LTD., Hubei (CN)

(72) Inventors: Fapu Chen, Wuhan (CN); Yuxin Shi, Wuhan (CN); Fakai Chen, Wuhan (CN)

(73) Assignee: WUHAN JIANMIN DAPENG PHARMACEUTICAL CO., LTD., Hubei (CN)

( * ) Notice: Subject to any disclaimer, the term of this patent is extended or adjusted under 35 U.S.C. 154(b) by 517 days.

(21) Appl. No.: 18/209,437

(22) Filed: Jun. 13, 2023

(65) Prior Publication Data

US 2023/0322671 A1 Oct. 12, 2023

Related U.S. Application Data

(63) Continuation-in-part of application No. PCT/CN2021/073780, filed on Jan. 26, 2021.

(30) Foreign Application Priority Data

Dec. 22, 2020 (CN) ........................ 202011526131.5

(51) Int. Cl.
*C07D 207/38* (2006.01)

(52) U.S. Cl.
CPC .................................. *C07D 207/38* (2013.01)

(58) Field of Classification Search
CPC ............................ C07D 501/46; C07D 207/38
See application file for complete search history.

(56) References Cited

U.S. PATENT DOCUMENTS

2016/0151535 A1 6/2016 Hoare et al.

FOREIGN PATENT DOCUMENTS

| | | | |
|---|---|---|---|
| CN | 106674075 | * 12/2016 | .......... C07D 207/38 |
| CN | 110092739 | * 6/2019 | .......... C07D 207/38 |
| WO | 03057131 | 7/2003 | |

OTHER PUBLICATIONS

Lombardi et al. Org. Biomol. Chem. (2017). vol 15, pp. 8218-8231.*
Jacobi et al., J. Org. Chem. (2000), vol. 65 pp. 8478-8489.*
Chiara Lombardi et al., "Recent advances in the synthesis of analogues of phytohormones strigolactones with ring-closing metathesis as a key step", Organic & Biomolecular Chemistry, vol. 15, Issue 38, Oct. 14, 2017, pp. 8218-8231.
RN 100383-27-5, Registry of STN, Feb. 22, 1986, pp. 1-6.
RN 771-80-2 Registry of STN, Nov. 16, 1984, pp. 1-6.
Peter A. Jacobi et al., "New Syntheses of the C,D-Ring Pyrromethenones of Phytochrome and Phycocyanin", The Journal of Organic Chemistry, vol. 65, Issue 25, Dec. 31, 2000, pp. 8478-8489.
Jan Grünewald et al., "Optimization of an Enzymatic Antibody-Drug Conjugation Approach Based on Coenzyme A Analogs", Bioconjugate Chemistry, vol. 28, Issue 7, Dec. 31, 2017, pp. 1906-1915.
"International Search Report (Form PCT/ISA/210) of PCT/CN2021/073780", mailed on Sep. 26, 2021, pp. 1-4.
"Written Opinion of the International Searching Authority (Form PCT/ISA/237) of PCT/CN2021/073780", mailed on Sep. 26, 2021, pp. 1-5.

* cited by examiner

*Primary Examiner* — Paul V Ward
(74) *Attorney, Agent, or Firm* — JCIP GLOBAL INC.

(57) ABSTRACT

A pyrrolinone compound represented by formula 1. $R_1$ is selected from one of $C_1$-$C_5$ alkoxy, benzyloxy, $C_1$-$C_5$ alkyl, or a phenyl group; $R_2$, $R_3$ at each occurrence independently represent hydrogen, $C_1$-$C_5$ alkyl, $C_1$-$C_5$ alkoxy, $C_1$-$C_5$ alkylthio, $C_1$-$C_5$ alkane sulfinyl, $C_1$-$C_5$ alkane sulfonyl, a substituted phenyl, a substituted phenoxy, a substituted phenylthio, a substituted phenylene sulfinyl, or a substituted benzene sulfonyl; and $n_1$, $n_2$ at each occurrence independently are an integer from 1 to 5.

19 Claims, No Drawings

PYRROLINONE COMPOUND AND METHOD FOR PREPARING THE SAME

CROSS-REFERENCE TO RELATED APPLICATIONS

This application is a continuation-in-part of International Patent Application No. PCT/CN2021/073780 with an international filing date of Jan. 26, 2021, designating the United States, now pending, and further claims foreign priority benefits to Chinese Patent Application No. 202011526131.5 filed Dec. 22, 2020. The contents of all the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, MA 02142.

BACKGROUND

The disclosure relates to a pyrrolinone compound and a method for preparing the same.

Pyrrolidone is an important structural segment of glimepiride, bilirubin, biliverdin, phycocyanin and other drugs and food additives.

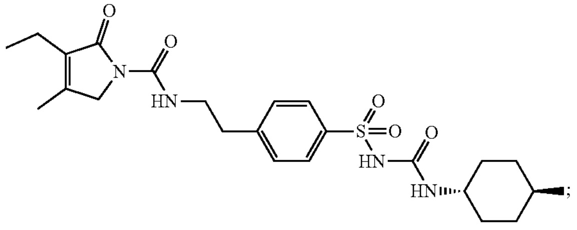

Glimepiride

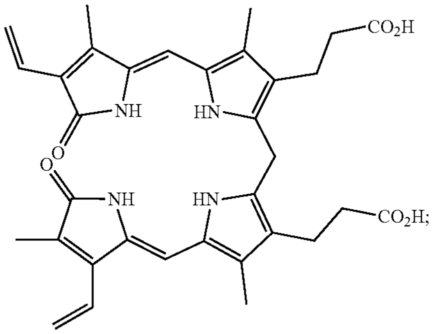

Bilirubin

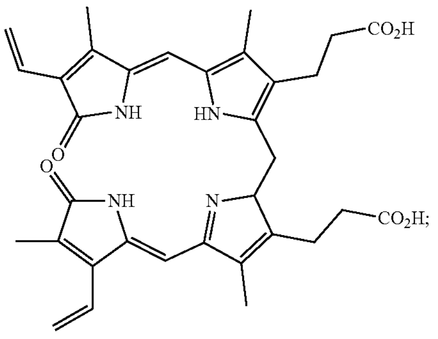

Biliverdin

-continued

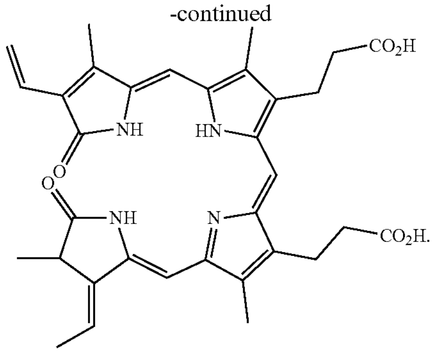

Phycocyanin

Conventional methods for preparing a pyrrolinone compound are described as follows:

1. With 1-tosylpyrrole as Starting Material

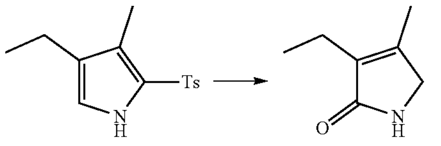

The method uses 1-tosylpyrrole as the raw material, through bromination, hydrolysis, reduction and other steps to obtain a pyrrolidone compound. During the hydrolysis process, a large amount of trifluoroacetic acid is consumed, leading to environmental pollution. Sodium borohydride is used for reduction, which is costly.

2. With Pyrrolamide as Starting Material

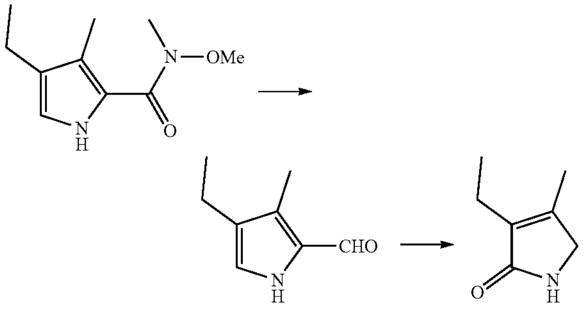

The method uses pyrrolamide as the raw material, which is reduced by lithium aluminum hydride to form pyrrolaldehyde, and then oxidized to produce pyrrolinone. The lithium aluminum hydride used in this method is expensive and dangerous, making it unsuitable for industrial production.

3. With Ethyl Acetoacetate as Starting Material

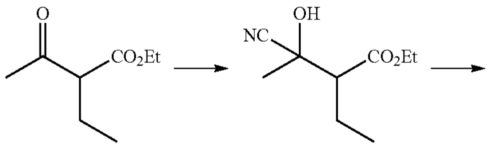

-continued

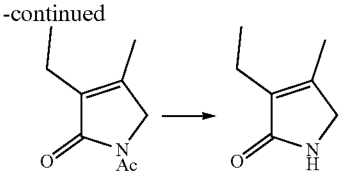

The method uses ethyl acetoacetate as the starting material, followed by addition of sodium cyanide, catalytic hydrogenation, and hydrolysis to obtain a pyrrolidone compound. The raw material used in this method, sodium cyanide, is highly toxic. Catalytic hydrogenation requires high pressure, with a yield of only 15%, which limits the industrial production.

4. With Acrylamide as Starting Material

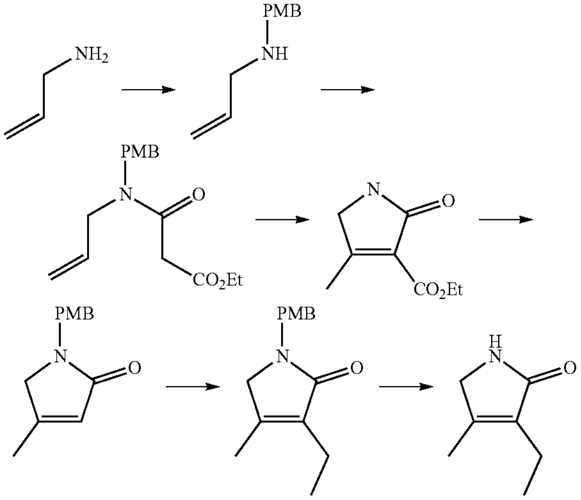

Compared with the above methods, the method involves no reagents such as lithium aluminum hydride, sodium cyanide, trifluoroacetic acid, and catalytic hydrogenation. However, reagents such as sodium borohydride and expensive palladium chloride are still required.

SUMMARY

To solve the aforesaid problems, the disclosure provides a pyrrolinone compound and a method for preparing the same.

The pyrrolinone compound represented by formula 1 is as follows:

1

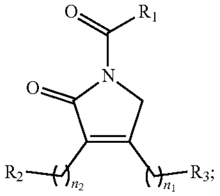

where, $R_1$ is selected from one of $C_1$-$C_5$ alkoxy, benzyloxy, $C_1$-$C_5$ alkyl, or a phenyl group; $R_2$, $R_3$ at each occurrence independently represent hydrogen, $C_1$-$C_5$ alkyl, $C_1$-$C_5$ alkoxy, $C_1$-$C_5$ alkylthio, $C_1$-$C_5$ alkane sulfinyl, $C_1$-$C_5$ alkane sulfonyl, a substituted phenyl, a substituted phenoxy, a substituted phenylthio, a substituted phenylene sulfinyl, or a substituted benzene sulfonyl; and $n_1$, $n_2$ at each occurrence independently are an integer from 1 to 5. The term "substituted" refers to substitutions at various positions, such as meta substitution, ortho substitution, para substitution, and further refers to different substituents, such as $C_1$-$C_5$ alkyl substitution, or halogen substitution.

In a class of this embodiment, $R_3$ is hydrogen, and $n_1$ is 1.

In a class of this embodiment, $n_2$ is 2.

In a class of this embodiment, the abovementioned compound has one of following formulas:

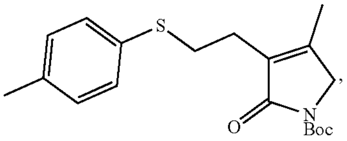

, and

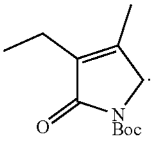

.

The disclosure also provides a method for preparing the abovementioned compound comprising applying a compound represented by formula 6 to synthesize the compound of formula 1:

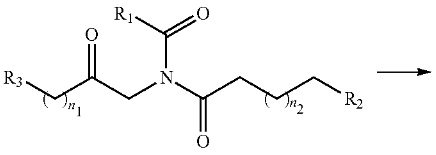

6

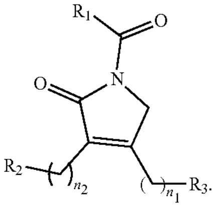

1

In a class of this embodiment, a starting compound is dissolved in a solvent and catalyzed by a base to yield the compound represented by formula 6.

In a class of this embodiment, the solvent is tetrahydrofuran, methanol, ethanol, water, acetone, dimethyl formamide (DMF), dimethylsulfoxide (DMSO), or a mixture thereof; and the base is sodium hydroxide, potassium hydroxide, sodium methoxide, sodium ethanol, potassium tert butanol, sodium tert butanol, 1,8-diazabicyclo (5.4.0) undec-7-ene (DBU), dimethylaminopyridine, or a mixture thereof.

In a class of this embodiment, the compound represented by formula 6 is prepared by a compound represented by formula 5 as follows:

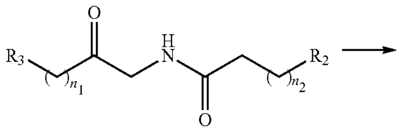

5

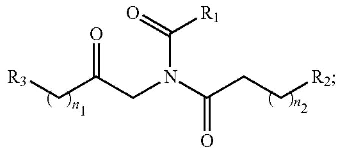

6

$R_1$ is selected from one of $C_1$-$C_5$ alkoxy, benzyloxy, $C_1$-$C_5$ alkyl, or a phenyl group; $R_2$, $R_3$ at each occurrence independently represent hydrogen, $C_1$-$C_5$ alkyl, $C_1$-$C_5$ alkoxy, $C_1$-$C_5$ alkylthio, $C_1$-$C_5$ alkane sulfinyl, $C_1$-$C_5$ alkane sulfonyl, a substituted phenyl, a substituted phenoxy, a substituted phenylthio, a substituted phenylene sulfinyl, or a substituted benzene sulfonyl; and $n_1$, $n_2$ at each occurrence independently are an integer from 1 to 5. The term “substituted” refers to substitutions at various positions, such as meta substitution, ortho substitution, para substitution, and further refers to different substituents, such as $C_1$-$C_5$ alkyl substitution, or halogen substitution.

In a class of this embodiment, the compound represented by formula 5 is dissolved in a solvent and reacts with an anhydride or acyl chloride in the presence of a base to yield the compound represented by formula 6.

In a class of this embodiment, the base is triethylamine, pyridine, dimethylaminopyridine, diisopropylethylamine, sodium carbonate, potassium carbonate, sodium bicarbonate, or a mixture thereof the solvent is dichloromethane, chloroform, tetrahydrofuran, acetone, and ethyl acetate, or a mixture thereof.

In a class of this embodiment, a molar ratio of the compound represented by formula 5 to the acyl chloride or anhydride to the base is 1:(0.8-2):(0.8-2).

In a class of this embodiment, the compound represented by formula 6 is prepared by the compound represented by formula 5 under a temperature of 0-30° C.

In a class of this embodiment, the compound represented by formula 5 is prepared by a compound represented by formula 4:

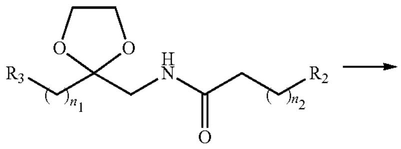

4

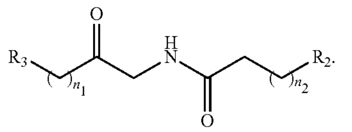

5

In a class of this embodiment, the compound represented by formula 4 is dissolved in a solvent and converted into the compound represented by formula 5 through a deprotection reaction in the presence of an acidity regulator.

In a class of this embodiment, the acidity regulator is hydrochloric acid, sulfuric acid, formic acid, acetic acid, or a mixture thereof and the solvent is dichloromethane, chloroform, tetrahydrofuran, acetone, and ethyl acetate, or a mixture thereof.

In a class of this embodiment, a molar ratio of the compound represented by formula 4 to the acidity regulator is between 1:0.1 and 1:1.

In a class of this embodiment, the compound represented by formula 5 is prepared by the compound represented by formula 4 under a temperature of 20-30° C.

In a class of this embodiment, the compound represented by formula 4 is prepared by reaction of a compound represented by formula 2 and a compound represented by formula 3 as follows:

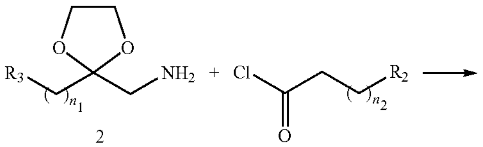

2

3

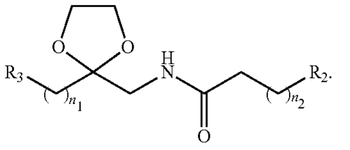

4

In a class of this embodiment, the compound represented by formula 2 and the compound represented by formula 3 are dissolved in a solvent and react with each other in the presence of a base to yield the compound represented by formula 4.

In a class of this embodiment, the solvent is dichloromethane, chloroform, tetrahydrofuran, acetone, and ethyl acetate, or a mixture thereof, and the base is triethylamine, pyridine, dimethylaminopyridine, diisopropylethylamine, sodium carbonate, potassium carbonate, sodium bicarbonate, or a mixture thereof.

In a class of this embodiment, a molar ratio of the compound represented by formula 2 to the compound represented by formula 3 to the base is 1:(0.8-2):(0.8-2).

In a class of this embodiment, the compound represented by formula 4 is prepared by reaction of the compound represented by formula 2 and the compound represented by formula 3 under a temperature of 15-30° C.

The following advantages are associated with the pyrrolinone compound and the method for preparing the same of the disclosure:

1. The pyrrolidone compound of the disclosure can be used as a pharmaceutical intermediate for preparing phycocyanin and glimepiride under mild conditions, with a higher yield than conventional methods.
2. The synthesis method for pyrrolidone compound of the disclosure is more suitable for industrialization, lower cost, and more mild synthesis conditions than conventional methods.

DETAILED DESCRIPTION

To further illustrate the disclosure, embodiments detailing a pyrrolinone compound and a method for preparing the same are described below. It should be noted that the following embodiments are intended to describe and not to limit the disclosure.

In the disclosure, NMR was measured using Bruker-AMX400 nuclear magnetic resonance instrument; ESI-MS was measured using Finnigan-MAT-95 mass spectrometer; all reagents are analytical pure (National Pharmaceutical Reagent Company). In the following examples, 2,2-dimethoxypropylamine is prepared according to the literature Eur. J. Med. Chem., 1995, 30, 931-942 method preparation; 4-p-Toluenesulfobutyryl chloride is prepared according to the method described in literature MedChemComm, 2017, 8, 1268-1274.

Example 1

Synthesis of Compound 4a: N-(2,2-dimethoxypropyl)-4-p-toluenesulfobutanamide 4a

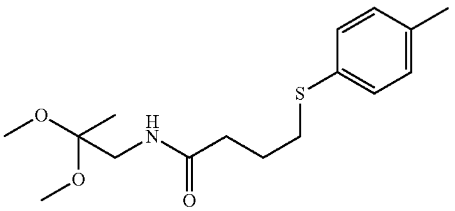

6.80 g of 2,2-dimethoxypropylamine (57.1 mmol) were weighed and dissolved in 20 mL of dichloromethane. Then, 6.10 g of triethylamine (60.4 mmol) was added to the resulting mixture and the mixture was cooled to 0° C. Thereafter, 13.03 g (57.1 mmol) of 4-p-toluenesulfobutyryl chloride dissolved in 20 mL of dichloromethane was slowly added to the mixture, and the temperature was controlled below 5° C. The mixture was stirred at 20-30° C. for 10 hours and filtered to obtain N-(2,2-dimethoxypropyl)-4-p-toluenesulfobutanamide. The filter cake was washed with dichloromethane, and the filtrate was used for next reaction.

Example 2

Synthesis of Compound 4b: N-(2,2-dimethoxypropyl) butanamide

4b

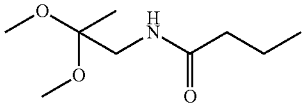

2,2-dimethoxypropylamine (55.8 mmol) was dissolved in 20 mL of tetrahydrofuran. Then, potassium carbonate (63.7 mmol) was added to the resulting mixture and the mixture was cooled to 0° C. Thereafter, 5.97 g (55.8 mmol) of butyryl chloride dissolved in 20 mL of tetrahydrofuran was slowly added to the mixture, and the temperature was controlled below 5° C. The mixture was stirred at 15-25° C. for 10 hours and filtered to obtain N-(2,2-dimethoxypropyl) butanamide. The filter cake was washed with dichloromethane, and the filtrate was used for next reaction.

Example 3

Synthesis of Compound 5a: N-acetone-4-p-toluenesulfobutylamide

5a

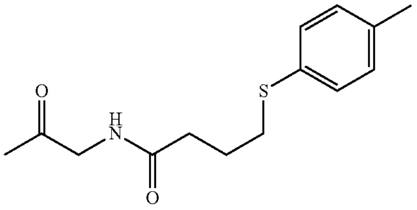

8.0 g (10.8 mmol) of 5% dilute hydrochloric acid was added to a dichloromethane solution containing the compound 4a obtained in Example 1. The mixture was stirred at 15-35° C. for 4 hours and rested. The separated dichloromethane layer was collected, washed with saturated salt water, water, dried over anhydrous sodium sulfate, filtered, concentrated, to yield 10.20 g of a white solid, that is, N-acetone-4-p-toluenesulfobutylamide. The two-step yield (the total yield of the two-step reaction in Example 1 and Example 3) is 96%. N-acetone-4-p-toluenesulfobutylamide: $^1$H NMR (400 MHz, $CDCl_3$): δ1.92-1.97 (m, 2H), 2.20 (s, 3H), 2.31 (s, 3H), 2.39 (t, 6.8 Hz, 2H), 2.93 (t, J=6.8 Hz, 2H), 4.14 (d, J=4.0 Hz, 2H), 6.22 (s, 1H), 7.09 (d, J=4.0 Hz, 2H), 7.26 (d, J=8.0 Hz, 2H); ESI-Mass: 266.0 $[M+H]^+$.

Example 4

Synthesis of Compound 5b: N-acetone-4-butylamide

5b

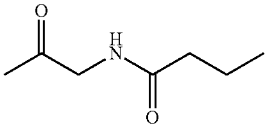

8.0 g of 5% dilute hydrochloric acid was added to a dichloromethane solution containing the compound 4b obtained in Example 2. The mixture was stirred at 15-35° C. for 4 hours and rested. The separated dichloromethane layer was collected, washed with saturated salt water, water, dried over anhydrous sodium sulfate, filtered, concentrated, to yield a white solid, that is, N-acetone-4-butylamide. The two-step yield (the total yield of the two-step reaction in Example 1 and Example 3) is 92%. N-acetone-4-butylamide: $^1$H NMR (400 MHz, $CDCl_3$): δ0.99 (t, J=7.0 Hz, 3H), 1.64-1.70 (m, 2H), 2.21 (s, 3H), 2.34 (t, J=6.8 Hz, 2H), 4.16 (s, 2H); ESI-Mass: 144.18 $[M+H]^+$.

Example 5

Synthesis of Compound 6a: N-acetonyl-N-tert-butyloxycarbonyl-4-p-toluenesulfobutylamide 6a

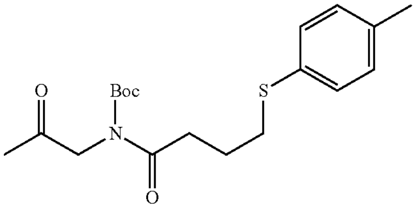

8 g of the compound 5a was dissolved in 50 mL of dichloromethane, and then 8.0 g of dimethylaminopyridine (DMAP) was added. The resulting mixture was cooled to 0° C., and 13.2 g of $Boc_2O$ dissolved in 90 mL of dichloromethane was added. The temperature was controlled to not exceed 5° C. The mixture was stirred at 15-30° C. for 10 hours and poured into 100 mL of ice water. The aqueous phase was acidified with dilute hydrochloric acid to pH 3. The organic layer was collected, washed with saturated sodium bicarbonate, salt water, dried over anhydrous sodium sulfate, filtered, and concentrated, to yield 10.81 g of light yellow liquid, which was N-acetonyl-N-tert-butyloxycarbonyl-4-p-toluenesulfobutylamide, with a yield of 99%. $^1$H NMR (400 MHz, $CDCl_3$): $\epsilon$ 1.47 (s, 9H), 1.93-1.97 (m, 2H), 2.14 (s, 3H), 2.30 (s, 3H), 2.93 (t, J=6.0 Hz, 2H), 3.08 (t, J=7.2 Hz, 2H), 4.49 (s, 2H), 7.08 (d, J=8.2 Hz, 2H), 7.25 (d, J=8.2 Hz, 2H); ESI-Mass: 387.97 $[M+Na]^+$.

Example 6

Synthesis of Compound 6b: N-acetone-N-tert butoxycarbonyl butylamide

6b

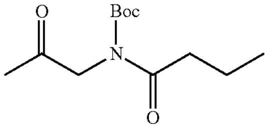

8 g of the compound 5b was dissolved in 50 mL of dichloromethane, and then 8.0 g of DMAP was added. The resulting mixture was cooled to 0° C., and 13.2 g of $Boc_2O$ dissolved in 90 mL of dichloromethane was added. The temperature was controlled to not exceed 5° C. The mixture was stirred at 15-35° C. for 10 hours and poured into 100 mL of ice water. The aqueous phase was acidified with dilute hydrochloric acid to pH 3. The organic layer was collected, washed with saturated sodium bicarbonate, salt water, dried over anhydrous sodium sulfate, filtered, and concentrated, to yield a light yellow oily product, which was N-acetone-N-tert butoxycarbonyl butylamide, with a yield of 97%. $^1$H NMR (400 MHz, $CDCl_3$): δ1.00 (t, J=7.2 Hz, 3H), 1.48 (s, 9H), 1.76-1.78 (m, 2H), 2.23 (s, 3H), 2.95 (m, 2H), 4.45 (s, 2H), ESI-Mass: 244.22 $[M+H]^+$.

Example 7

Synthesis of Compound 1a: N-tert butoxycarbonyl-3-(2-p-tolylthioethyl)-4-methyl-1H-2 (5H) pyrrolidone 1a

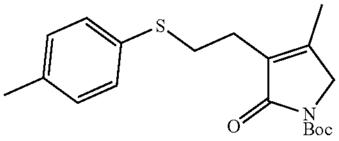

6.80 g of the compound 6a was dissolved in 50 mL of dimethylsulfoxide (DMSO) containing 3.0 g of sodium hydroxide, stirred at 15-35° C. for 30 minutes. The resulting mixture was poured into 100 mL of ice water, extracted with ethyl acetate, washed with dilute hydrochloric acid to neutral, washed with saturated salt water, dried with anhydrous sodium sulfate, filtered, concentrated, and recrystallized with ethanol to obtain 6.0 g of an earthy yellow solid with a yield of 84%. $^1$H NMR (400 MHz, $CDCl_3$): δ1.55 (s, 9H), 1.95 (s, 3H), 2.30 (s, 3H), 2.57 (t, J=7.2 Hz, 2H), 3.11 (t, J=7.2 Hz, 2H), 4.03 (s, 2H), 7.08 (d, J=8.0 Hz, 2H), 7.25 (d, J=8.0 Hz, 2H); ESI-Mass: 717.14 $[2M+Na]^+$.

Example 8

Synthesis of Compound 1b: N-tert butoxycarbonyl-3-ethyl-4-methyl-1H-2 (5H) pyrrolidone 1b

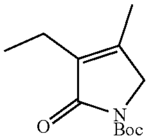

6.80 g of the compound 6b was dissolved in 50 mL of DMSO containing 3.0 g of sodium hydroxide, stirred at 15-35° C. for 30 minutes. The resulting mixture was poured into 100 mL of ice water, extracted with ethyl acetate, washed with dilute hydrochloric acid to neutral, washed with saturated salt water, dried with anhydrous sodium sulfate, filtered, concentrated, and recrystallized with ethanol to obtain a colorless oily product, that is, N-tert butoxycarbonyl-3-ethyl-4-methyl-1H-2 (5H) pyrrolidone, with a yield of 77%. $^1$H NMR (400 MHz, $CDCl_3$): δ1.10 (t, J=7.0 Hz, 3H), 1.49 (s, 9H), 2.01 (s, 3H), 2.32 (q, J=7.4 Hz, 2H), 4.20 (s, 2H), ESI-Mass: 226.22 $[M+1]^+$.

Example 9

Synthesis of an Intermediate of Phycocyanin with Compound 1a

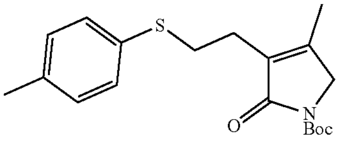
+

-continued

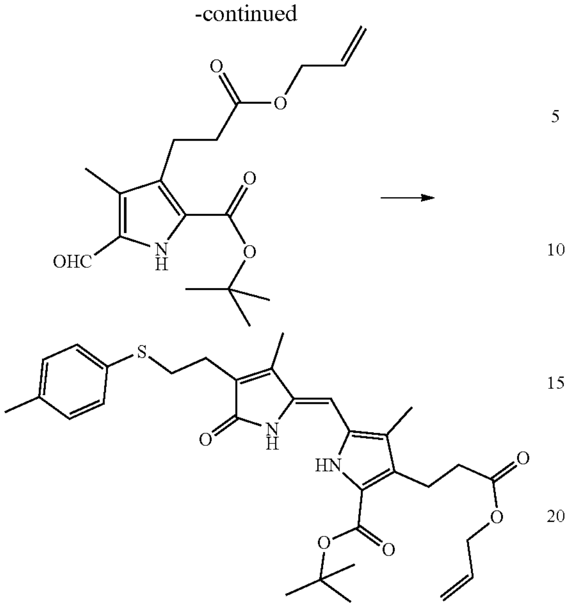

3.47 g of the compound shown in formula 1a and 3.21 g of 5-formyl-4-methyl-3-allyloxycarbonyl-ethyl-2 tert-butyl pyrrolite were mixed and dissolved in 30 mL of toluene. 5.0 g of DBU was added to the resulting mixture, heated and refluxed for 2 hours, and vacuum distillation was performed to remove the solvent. The residue was recrystallized with 20 mL of methanol to obtain 4.12 g of a yellow solid with a yield of 75%. The spectral data are the same as Synlet 1999, 51, 901-904.

Example 10

Synthesis of an Intermediate of Glimepiride with Compound 1b

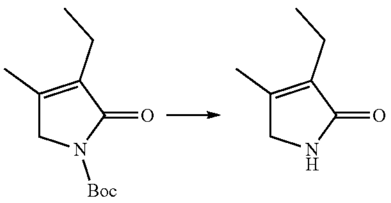

1.12 g of the compound shown in formula 1b was dissolved in 10 mL of ethyl acetate, cooled to 0° C., and 10 mL of 4 N hydrochloric acid dissolved in 15 mL of dioxane was slowly added to the resulting mixture. The temperature was slowly raised to 15-35° C., and the mixture was stirred for 2 hours, extracted with ethyl acetate, washed with saturated salt water, dried with anhydrous sodium sulfate, and separated through column chromatography to obtain 0.46 g of a white solid, with a yield of 75%. Spectral data is the same as Synthesis, 2015; 47, 955-960.

It will be obvious to those skilled in the art that changes and modifications may be made, and therefore, the aim in the appended claims is to cover all such changes and modifications.

What is claimed is:

1. A pyrrolinone compound represented by formula 1:

1

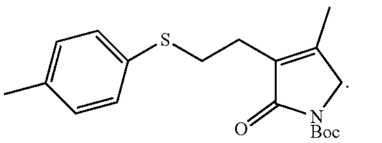

2. A method for preparing the compound of claim 1, comprising dissolving a compound represented by formula 6 in a solvent containing a base to synthesize the compound of formula 1:

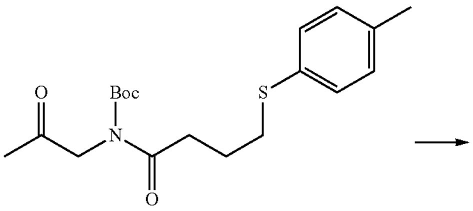

6

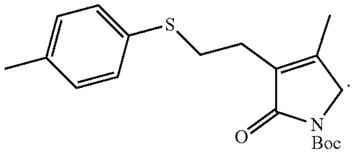

1

3. The method of claim 2, wherein a starting compound is dissolved in the solvent and catalyzed by the base to yield the compound represented by formula 6.

4. The method of claim 3, wherein the solvent is tetrahydrofuran, methanol, ethanol, water, acetone, dimethyl formamide (DMF), dimethylsulfoxide (DMSO), or a mixture thereof; and the base is sodium hydroxide, potassium hydroxide, sodium methoxide, sodium ethanol, potassium tert butanol, sodium tert butanol, 1,8-diazabicyclo(5.4.0) undec-7-ene (DBU), dimethylaminopyridine, or a mixture thereof.

5. The method of claim 2, wherein the compound represented by formula 6 is prepared by a compound represented by formula 5 as follows:

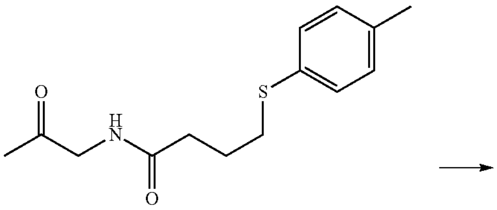

5

-continued

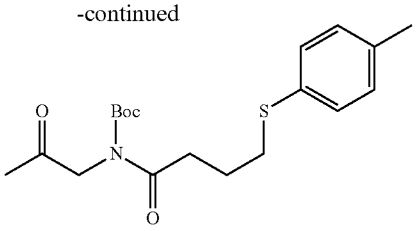

6

6. The method of claim 5, wherein the compound represented by formula 5 is dissolved in a solvent and reacts with an anhydride or acyl chloride in the presence of a base to yield the compound represented by formula 6.

7. The method of claim 6, wherein the base is triethylamine, pyridine, dimethylaminopyridine, diisopropylethylamine, sodium carbonate, potassium carbonate, sodium bicarbonate, or a mixture thereof; the solvent is dichloromethane, chloroform, tetrahydrofuran, acetone, and ethyl acetate, or a mixture thereof.

8. The method of claim 6, wherein a molar ratio of the compound represented by formula 5 to the anhydride or acyl chloride to the base is 1:(0.8-2):(0.8-2).

9. The method of claim 5, wherein the compound represented by formula 6 is prepared by the compound represented by formula 5 under a temperature of 0-40° C.

10. The method of claim 5, wherein the compound represented by formula 5 is prepared by a compound represented by formula 4:

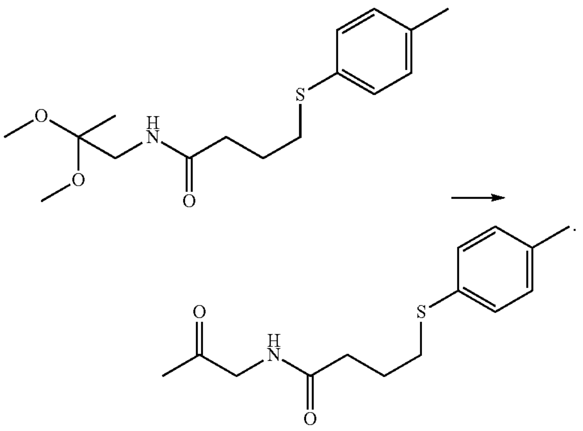

5

11. The method of claim 10, wherein the compound represented by formula 4 is dissolved in a solvent and converted into the compound represented by formula 5 through a deprotection reaction in the presence of an acidity regulator.

12. The method of claim 11, wherein the acidity regulator is hydrochloric acid, sulfuric acid, formic acid, acetic acid, or a mixture thereof; and the solvent is dichloromethane, chloroform, tetrahydrofuran, acetone, and ethyl acetate, or a mixture thereof.

13. The method of claim 12, wherein a molar ratio of the compound represented by formula 4 to the acidity regulator is between 1:0.1 and 1:1.

14. The method of claim 10, wherein the compound represented by formula 5 is prepared by the compound represented by formula 4 under a temperature of 20-30° C.

15. The method of claim 10, wherein the compound represented by formula 4 is prepared by reaction of a compound represented by formula 2 and a compound represented by formula 3 as follows:

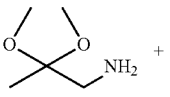

2

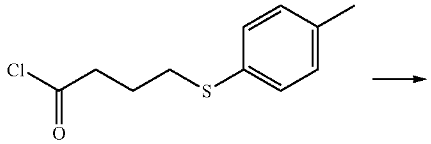

3

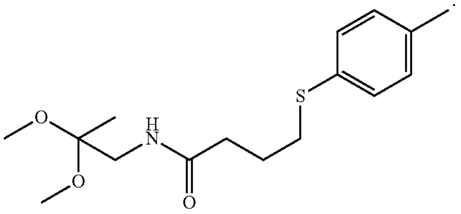

4

16. The method of claim 15, wherein the compound represented by formula 2 and the compound represented by formula 3 are dissolved in a solvent and react with each other in the presence of a base to yield the compound represented by formula 4.

17. The method of claim 16, wherein the solvent is dichloromethane, chloroform, tetrahydrofuran, acetone, ethyl acetate, or a mixture thereof, and the base is triethylamine, pyridine, dimethylaminopyridine, diisopropylethylamine, sodium carbonate, potassium carbonate, sodium bicarbonate, or a mixture thereof.

18. The method of claim 16, wherein a molar ratio of the compound represented by formula 2 to the compound represented by formula 3 to the base is 1:(0.8-2):(0.8-2).

19. The method of claim 15, wherein the compound represented by formula 4 is prepared by reaction of the compound represented by formula 2 and the compound represented by formula 3 under a temperature of 15-30° C.

* * * * *